(12) United States Patent
Bais et al.

(10) Patent No.: US 12,378,166 B2
(45) Date of Patent: Aug. 5, 2025

(54) INCREASING WATER RETENTION IN SOIL TO MITIGATE DROUGHT

(71) Applicants: Harsh Bais, Newark, DE (US); Yan Jin, Newark, DE (US)

(72) Inventors: Harsh Bais, Newark, DE (US); Yan Jin, Newark, DE (US)

(73) Assignee: University of Delaware, Newark, DE (US)

( * ) Notice: Subject to any disclaimer, the term of this patent is extended or adjusted under 35 U.S.C. 154(b) by 960 days.

(21) Appl. No.: 17/045,010

(22) PCT Filed: Apr. 3, 2019

(86) PCT No.: PCT/US2019/025500
§ 371 (c)(1),
(2) Date: Oct. 2, 2020

(87) PCT Pub. No.: WO2019/195365
PCT Pub. Date: Oct. 10, 2019

(65) Prior Publication Data
US 2021/0145008 A1 May 20, 2021

Related U.S. Application Data

(60) Provisional application No. 62/651,753, filed on Apr. 3, 2018.

(51) Int. Cl.
| | |
|---|---|
| *C05D 9/00* | (2006.01) |
| *A01N 25/08* | (2006.01) |
| *A01N 63/22* | (2020.01) |
| *C09K 17/16* | (2006.01) |
| *C12N 1/20* | (2006.01) |
| *C12R 1/125* | (2006.01) |

(52) U.S. Cl.
CPC .............. *C05D 9/00* (2013.01); *A01N 25/08* (2013.01); *A01N 63/22* (2020.01); *C09K 17/16* (2013.01); *C12N 1/205* (2021.05); *C12R 2001/125* (2021.05)

(58) Field of Classification Search
CPC .......... C05D 9/00; A01N 25/08; A01N 63/22; C09K 17/16; C12N 1/205; C12N 1/20; C12R 2001/125
See application file for complete search history.

(56) References Cited

U.S. PATENT DOCUMENTS

2011/0212835 A1* 9/2011 Bais ..................... A01N 63/22
504/117

OTHER PUBLICATIONS

Kroener et al. (Effects of Mucilage on Rhizosphere Hydraulic Functions Depend on Soil Particle Size, Vadose Zone Journal, Feb. 15, 2018). (Year: 2018).*
Vardharajula et al (Exopolysaccharide Production by Drought Tolerance Bacillus Spp. And Effect on Soil Aggregation Under Drought Stress, JMBFS, 2014 (Year: 2014).*
Eshel et al., Soil Sci. Soc. Am., 2004, 68:736-743.
Kroener et al., Vadose Zone Journal, Feb. 15, 2018, 11 pages.
Kumar et al., The Plane Journal, 2012, 72(4), pp. 694-706.
Peters et al., Water Resources Research, 2008, vol. 44, W11417, 11 pages.
Simunek et al., Soil Sci. Soc. Am, 1998, 62(4), pp. 894-905.
Zheng et al., American Geophysical Union, Fall Meeting 2017, Dec. 2017, 2 pages. (Abstract only).
Zheng et al., Water Resources Research, Apr. 19, 2018, pp. 3673-3687.
International Search Report and Written Opinion for International Application PCT/US2019/025550, dated Jun. 20. 2019, 10 pages.
Gee et al., (Sssa Book Series No. 6), 2002, pp. 3873-411.
Klute et al., Methods of Soil Analysis: Part 1 Physical and Mineralogical Methods, 1986, 5.1, Second Edition, pp. 687-734.
Lehmann et al., Physical Review E, 77(5), 056309 (2008).
Peters et al., Journal of Hydrology, 527, pp. 531-542 (2015).
International Preliminary Report on Patentability and Written Opinion for International Application No. PCT/US2019/025500, issued Oct. 6, 2020, 9 pages.

* cited by examiner

*Primary Examiner* — Robert A Wax
*Assistant Examiner* — John Seungjai Kwon
(74) *Attorney, Agent, or Firm* — Buchanan Ingersoll & Rooney PC

(57) ABSTRACT

The present invention provides a soil composition having improved water retention. The composition comprises soil particles and *Bacillus subtilis* UD1Q22. For example, the composition may comprise soil particles having a particle size no greater than 2 mm and at least 50% of the soil particles have a particle size in the range of 0.05-2 mm. A method for improving water retention of a soil composition is also provided. The method comprises applying an effective amount of *Bacillus subtilis* UD1022 to the soil composition to improve water retention of the soil composition.

17 Claims, 6 Drawing Sheets

INCREASING WATER RETENTION IN SOIL TO MITIGATE DROUGHT

CROSS-REFERENCE TO RELATED APPLICATION

This application is a U.S. national phase of International Application No. PCT/US2019/025500, filed Apr. 3, 2019, claiming priority to U.S. Provisional Application No. 62/651,753, filed Apr. 3, 2018, the contents of which are incorporated herein by reference in their entireties for all purposes.

FIELD OF THE INVENTION

The invention relates generally to enhancement of plant drought stress tolerance by improving soil water retention with plant growth-promoting rhizobacteria (PGPR), for example, *Bacillus subtilis* UD1022.

BACKGROUND OF THE INVENTION

Global food security is an increasing concern worldwide. Increasing global population and consumption are placing unprecedented demand on agriculture for food production. A key challenge facing the agricultural sector to secure food availability is global water shortage and degradation, which are already limiting crop yield today and the limitation will further intensify as agricultural activities expand to less fertile areas. Over 50% of the population increase expected by 2050 will take place in Sub-Saharan Africa, with another 30% in South and Southeast Asia—the same places projected to suffer most from climate change. In the United States, California—and its $54 billion agricultural industry—has recently experienced its worst drought in 500 years. In 2014 alone, the state shed $2.2 billion and thousands of jobs from the agricultural sector due to the ongoing drought, while water supplies, arable land, and soil integrity continued to decline. The problem is global in scale for food markets and the associated economic growth can cause regional tension. Therefore, developing novel solutions for plant growth under restricted water availability is of central significance.

An emerging perspective on optimizing the availability and productive flow of green water provides options for meeting future demands on global food production. Green water, which is hydrologically complementary to blue water (i.e., water stored in lakes and reservoirs or is pumped from aquifers), refers to water in soil that remains potentially available to plants and the soil biota after precipitation losses to runoff and deep percolation have occurred. On the one hand, because nearly 90% of the water consumed by croplands worldwide is green water, optimizing green water use without overexploitation of blue water resources thus provides opportunities to promote plant growth. On the other hand, water loss from cropland includes evaporation and plant transpiration. Given the positive correlation between transpiration and plant growth, only transpiration is considered as productive green water flow; the percentage of the productive flow depends on the efficacy of the rhizosphere (i.e. the narrow region of soil that is directly influenced by root secretions and associated soil microorganisms) in promoting transpiration over evaporation in addition to intrinsic characteristics of the plants grown. Both hydrologic master variables, i.e., green water availability and productive green water flow, highlight the importance of the rhizosphere as the interface supporting the exchange of water and nutrients between plants and their associated soil environment through which all productive green water must pass.

Rhizosphere, as the interface between plant roots and soil matrix, is rich in nutrients and provides a unique environment for large and diverse communities of microbes, including plant growth promoting rhizobacteria (PGPR). The beneficial role of PGPR in plant growth through nitrogen fixation and biocontrol has been well established; enhancement of plant drought stress tolerance by PGPR has also been increasingly documented in the literature. Plant drought tolerance enhancement by PGPR was first reported based on observation that *Arabidopsis thaliana* inoculated with PGPR *Paenibacillus polymyxa* B2 could survive drought stress much longer than untreated control plants. Subsequently, PGPR was also found to increase resistance to water stress in tomatoes and peppers, in common bean (*Phaseolus vulgaris* L.), in *Arabidopsis*, in wheat, and in maize.

Investigations on the mechanisms by which PGPR mediate plant drought tolerance have largely focused on PGPR-root/plant interactions and related plant responses to PGPR activities. Comparatively, much less is known about PGPR's role in mediating physiochemical and hydrological changes in the rhizospheric soil that may impact plant drought stress tolerance. PGPR are soil bacteria that are generally embedded in biofilms (i.e., aggregates or stationary colonies) formed by biosynthesized extracellular polymeric substances (EPS). EPS possess large water holding capacity and become hydrophobic when they are dried, and thus can influence soil water retention characteristics and hydraulic conductivity by modifying structural and physicochemical properties of the rhizospheric soil and consequently change plant water-use efficiency. Several studies showed that EPS or their chemical analogs increased soil water content and reduced hydraulic conductivity under saturated or partially saturated conditions, implying a potential increase in green water availability and productive flow.

The effects of EPS on soil water retention and hydraulic properties point to PGPR's potential role in increasing green water availability and productive flow through mediating positive feedbacks in plant-microbe-soil terrestrial systems. However, the underlying mechanisms of PGPR's effects on modifying soil's hydraulic properties remain poorly understood. In addition, how soil evaporation, as one of the two components in the evapotranspiration process and a key factor in determining the magnitude of productive green water flow, is affected by the presence of PGPR remains an unanswered question. The effects of bacterial EPS on evaporation of water in a micromodel system composed of two-dimensional structures were studied, and it was found that water evaporated more slowly from the microchannel filled with EPS-producing bacteria compared to the channel with non-EPS-producing bacteria. Water evaporation from EPS was also measured in the absence of the 2D structure, and it was found that the synergistic effects of soil structure were essential for EPS to produce evaporative resistance. No direct evaluation of the effects of PGPR has been reported on evaporation at the Darcy scale with soil or similar porous materials.

The effects of PGPR are different for different textured soils thus there remains a need for a soil textural composition with increased water retention and a method for increasing water retention of a soil textural composition.

SUMMARY OF THE INVENTION

The present invention relates to a soil composition having improved water retention and a method for improving water retention of a soil composition. The terms "soil composition" and "soil textural composition" are used herein interchangeably.

A soil composition is provided. The soil composition comprises at least 80 wt % soil particles having a particle size no greater than 2 mm and at least 0.1 wt % *Bacillus subtilis* UD1022, each based on the total weight of the soil composition. At least 50% of the soil particles have a particle size in the range of 0.05-2 mm.

The *Bacillus subtilis* UD1022 may be in an amount effective for increasing water content of the soil composition as compared with a control composition. The *Bacillus subtilis* UD1022 may be in an amount effective for reducing unsaturated hydraulic conductivity of the soil composition as compared with a control composition. The *Bacillus subtilis* UD1022 may be in an amount effective for reducing water evaporation rate of the soil composition as compared with a control composition.

The at least 50 wt % of the particles may have a particle size in the range of 1-2 mm. The at least 50 wt % of the particles may have a particle size in the range of 1-0.5 mm. The at least 50 wt % of the particles may have a particle size in the range of 0.25-0.5 mm. The at least 50 wt % of the particles may have a particle size in the range of 0.1-0.25 mm. The at least 50 wt % of the particles may have a particle size in the range of 0.05-0.1 mm.

The soil composition may have a soil texture selected from the group consisting of sand, loamy sand, sandy loam, loam, silt loam and silt.

A method for improving water retention of a soil composition is provided. The soil composition comprises at least 80 wt % soil particles having a particle size no more than 2 mm and at least 50% of the soil particles have a particle size in the range of 0.05-2 mm. The method comprises applying to the soil composition *Bacillus subtilis* UD1022 in an amount effective for improving water retention of the soil composition.

The method may further comprise increasing water content of the soil composition. The method may further comprise reducing unsaturated hydraulic conductivity of the soil composition. The method may further comprise reducing water evaporation rate of the soil composition.

According to the method of the present invention, the at least 50 wt % of the particles may have a particle size in the range of 1-2 mm, 1-0.5 mm, 0.25-0.5 mm, 0.1-0.25 mm or 0.05-0.1 mm. The soil composition may have a soil texture selected from the group consisting of sand, loamy sand, sandy loam, loam, silt loam and silt.

DETAILED DESCRIPTION OF THE INVENTION

Figure 1:
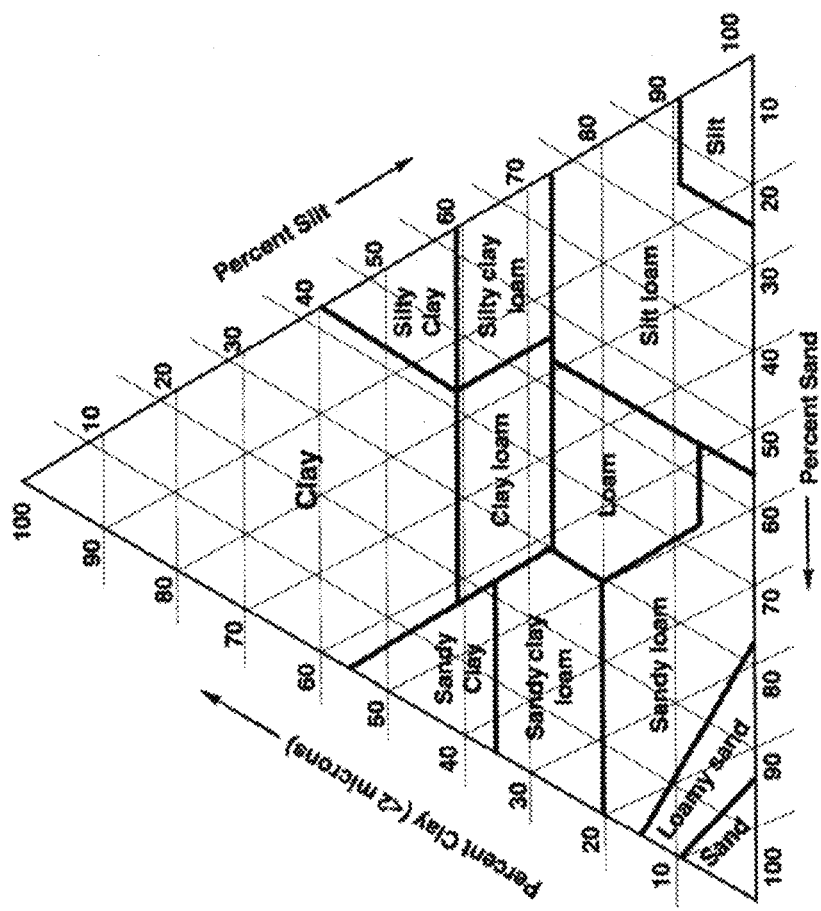
FIG. 1 shows a soil triangle indicating particle size distribution of soil samples having different textures.

The present invention relates to a soil composition having improved water retention and a method for improving water retention of a soil composition. The invention is made based on the surprising discovery that sandy soils and clay soils treated with *Bacillus subtilis* strain UD1022 (*B. subtilis* UD1022 or *Bacillus subtilis* UD1022) held more water and showed reduced hydraulic conductivity and accumulative evaporation, as compared with their corresponding controls.

Unless stated otherwise, a wt % figure for an ingredient of a composition is relative to the total weight of the composition.

Soil is the upper layer of earth in which plants and other organisms grow. Soil particles are natural entities of soil of various sizes including sand, silt and clay, and may exist as separate tiny units or clumped together in crumbs. Soil contains soil particles of different sizes. The term "particle size" as used herein refers to the average particle size of a particle. The spaces between the soil particles and/or crumbs are pores. Ideally, pore spaces in soil are large enough to leave room for air and allow excess water to drain away, and small enough to hold sufficient water for growth of plants and other organisms.

Soil particles are generally defined by their sizes. Sand particles are soil particles having a particle size of 0.05-2.00 mm. Silt particles are soil particles having a particle size of 0.002-0.05 mm. Clay particles are soil particles having a particle size less than 0.002 mm. Convention techniques known in the art, for example, sieving, sedimentation hydrometer method, and pipette method (Gee and Or, Particle size analysis. In Methods of Soil Analysis, Part 1—Physical and Mineralogical Analysis, SSSA Book Series No. 5, 2002, p. 383-411), laser diffraction particle sizing (Eshel et al., 2004, Critical evaluation of the laser diffraction for particle-size distribution analysis. Soil Sci. Soc. Am. J. 68:736-743), may be used to determine soil particle sizes.

A soil sample may be characterized by weight percentages of soil particles having different sizes in the soil sample. The term "soil texture" as used herein refers to soil particle size distribution of a soil sample, i.e., weight percentages of soil particles of different sizes in a soil sample. The physical and chemical properties of a soil sample may be affected by a change in its soil texture. Soil texture is an important characteristic of a soil sample that may influence water absorption, water retention, tillage operation, aeration status and fertility of the soil sample. In general, a soil sample having fine particles and small pore spaces retain more water than a soil sample having larger particles and large pore spaces. The U.S. Department of Agriculture defines 12 soil texture groups (i.e., sand, loamy sand, sandy loam, loam, silt loam, silt, sandy clay loam, clay loam, silty clay loam, sandy clay, silty clay and clay) for a soil sample based on weight percentages of sand, silt and clay particles in the soil sample.

The term "soil water retention" as used herein refers to the ability to retain water by a soil sample. Soil water retention may vary depending on the nature of the soil sample, for example, its soil texture and ingredients. Improvement of soil water retention, especially for a soil sample having poor soil water retention, is important to mitigation of drought and increase land productivity and soil health for plants and other organisms in the soil. Improvement of soil water retention of a soil sample may be evidenced by an increase in water content of the soil sample. An increase in water content may be a result of improved water retention or addition of more water. Improving water retention may encompass keeping water in a soil sample longer.

The term "unsaturated hydraulic conductivity" as used herein refers to the rate at which water moves through a soil sample under unsaturated conditions (i.e., when soil pores are not completely filled with water). Reduction of unsaturated hydraulic conductivity of a soil sample may be associated with improvement of water retention of a soil sample.

The term "water evaporation rate" as used herein refers to the rate at which water is lost from a soil sample by evaporation. Reduction of water evaporation rate of a soil sample may be associated with improvement of water retention of a soil sample.

The present invention provides a soil textural composition. The soil composition comprises soil particles and *Bacillus subtilis* UD1022. The soil composition may have improved water retention as compared with a control composition. The control composition is identical to the soil composition except that the control composition does not comprise the *Bacillus subtilis* UD1022.

The soil particles in the soil composition may constitute at least 50, 60, 70, 80, 90, 95 or 99 wt %, or 50-99, 50-90, 50-80, 50-70, 50-60, 60-99, 60-90, 60-80, 60-70, 70-99 or 70-80 wt % of the soil composition. The soil particles may have a particle size no greater than 0.05, 0.1, 0.2, 0.25, 0.3, 0.4, 0.5, 0.6, 0.7, 0.75, 0.8, 0.9, 1, 1.5 or 2 mm. The soil particles may have a particle size no less than 0.05, 0.1, 0.2, 0.25, 0.3, 0.4, 0.5, 0.6, 0.7, 0.75, 0.8, 0.9, 1, 1.5 or 2 mm. The soil particles may have a particle size in the range of 0.05-0.1, 0.05-0.25, 0.05-0.25 0.05-0.5, 0.05-1, 0.05-2, 0.1-0.25, 0.1-0.5, 0.1-1, 0.1-2, 0.25-0.5, 0.25-1.0, 0.25-2, 0.5-1, 0.5-2 or 1-2 mm.

At least 50, 60, 70, 80, 90, 95 or 99% of the soil particles in the soil composition may have a particle size no greater than 0.05, 0.1, 0.2, 0.25, 0.3, 0.4, 0.5, 0.6, 0.7, 0.75, 0.8, 0.9, 1, 1.5 or 2 mm. At least 50, 60, 70, 80, 90, 95 or 99% of the soil particles in the soil composition may have a particle size no less than 0.05, 0.1, 0.2, 0.25, 0.3, 0.4, 0.5, 0.6, 0.7, 0.75, 0.8, 0.9, 1, 1.5 or 2 mm. At least 50, 60, 70, 80, 90, 95 or 99% of the soil particles in the soil composition may have a particle size in the range of 0.05-0.1, 0.05-0.25, 0.05-0.25 0.05-0.5, 0.05-1, 0.05-2, 0.1-0.25, 0.1-0.5, 0.1-1, 0.1-2, 0.25-0.5, 0.25-1.0, 0.25-2, 0.5-1, 0.5-2 or 1-2 mm.

Soil particles having a particle size no greater than 0.05, 0.1, 0.2, 0.25, 0.3, 0.4, 0.5, 0.6, 0.7, 0.75, 0.8, 0.9, 1, 1.5 or 2 mm may constitute 50, 60, 70, 80, 90, 95 or 99 wt % of the soil composition. Soil particles having a particle size no less than 0.05, 0.1, 0.2, 0.25, 0.3, 0.4, 0.5, 0.6, 0.7, 0.75, 0.8, 0.9, 1, 1.5 or 2 mm may constitute 50, 60, 70, 80, 90, 95 or 99 wt % of the soil composition. Soil particles having a particle size in the range of 0.05-0.1, 0.05-0.25, 0.05-0.25 0.05-0.5, 0.05-1, 0.05-2, 0.1-0.25, 0.1-0.5, 0.1-1, 0.1-2, 0.25-0.5, 0.25-1.0, 0.25-2, 0.5-1, 0.5-2 or 1-2 mm may constitute 50, 60, 70, 80, 90, 95 or 99 wt % of the soil composition. In one embodiment, the soil composition may comprise at least 80 wt % soil particles having a particle size no greater than 2 mm and at least 50% of such soil particles have a particle size in the range of 0.05-2 mm.

The soil composition may have a soil texture selected from the group consisting of sand, loamy sand, sandy loam, loam, silt loam and silt. Exemplary soil textures may be found in the soil triangle (FIG. 1). For example, a soil composition having a soil texture of sand may comprise about 92-100 wt % sand particles, about 0-18 wt % silt particles and about 0-10 wt % clay particles. A soil composition having a soil texture of loamy sand may comprise about 77-92 wt % sand particles, about 0-33 wt % silt particles and about 10-15 wt % clay particles. A soil composition having a soil texture of sandy loam may comprise about 50-95 wt % sand particles, about 0-53 wt % silt particles and about 15-20 wt % clay particles. A soil composition having a soil texture of loam may comprise about 40-70 wt % sand particles, about 30-53 wt % silt particles and about 7-27 wt % clay particles. A soil composition having a soil texture of silt loam may comprise about 20-55 wt % sand particles, about 55-83 wt % silt particles and about 0-27 wt % clay particles. A soil composition having a soil texture of silt may comprise about 0-25 wt % sand particles, about 85-100 wt % silt particles and about 0-10 wt % clay particles.

*Bacillus subtilis* UD1022 may constitute at least 0.01, 0.05, 0.1, 0.5, 1.0, 1.5, 2.0, 2.5, 3.0, 3.5, 4.0, 4.5, 5.0, 5.5 or 10 wt %, or 0.01-10, 0.01-5, 0.01-1, 0.01-0.05, 0.1-10, 0.1-5, 0.1-1, 1-10 or 1-5 wt % of the soil composition. The soil composition may comprise the at least $10^5$, $10^6$, $10^7$, $10^8$ or $10^9$, or $10^5$-$10^{11}$, $10^6$-$10^{10}$ or $10^7$-$10^9$, *Bacillus subtilis* UD1022 cells per gram of the soil composition. At least 50, 60, 70, 80, 90, 95 or 99% of the *Bacillus subtilis* UD1022 cells may be viable.

The soil composition may have improved water retention as compared with a control composition. The water retention of the soil composition may be as least 1, 2, 3, 4, 5, 10, 15, 20, 25, 30, 35, 40, 45, 50, 55, 60, 65, 70, 75, 80, 85, 90, 95, 99, 100 or 200% higher than that of the water retention of the control composition.

The term "an effective amount" refers to an amount of *Bacillus subtilis* UD1022 in the soil composition required to achieve a stated goal (e.g., improving water retention, increasing water content, reducing unsaturated hydraulic conductivity, and/or reducing water evaporation rate). The effective amount of *Bacillus subtilis* UD1022 in a soil composition may vary depending upon the stated goals and the physical characteristics of the soil composition. The specific amount of *Bacillus subtilis* UD1022 in the soil composition may be set based on the soil texture of the soil composition.

The soil composition may comprise an effective amount of *Bacillus subtilis* UD1022 for increasing water content of the soil composition as compared with a control composition by, for example, as least 1, 2, 3, 4, 5, 10, 15, 20, 25, 30, 35, 40, 45, 50, 55, 60, 65, 70, 75, 80, 85, 90, 95, 99, 100 or 200%, or 1-5, 1-10, 1-20, 1-30, 1-40, 1-50, 1-60, 1-70, 1-80, 1-90, 5-10, 5-20, 5-30, 5-40, 5-50, 5-60, 5-70, 5-80, 5-90, 10-20, 10-30, 10-40, 10-50, 10-60, 10-70, 10-80, 10-90, 20-30, 20-40, 20-50, 20-60, 20-70, 20-80, 20-90, 30-40, 30-50, 30-60, 30-70, 30-80, 30-90, 40-50, 40-60, 40-70, 40-80 or 40-90%. In one embodiment, the soil composition may comprise an effective amount of *Bacillus subtilis* UD1022 for increasing water content of the soil composition as compared with a control composition by at least 5-50%. The effective amount of *Bacillus subtilis* UD1022 for increasing water content of the soil composition may be at least 0.01, 0.05, 0.1, 0.5, 1.0, 1.5, 2.0, 2.5, 3.0, 3.5, 4.0, 4.5, 5.0, 5.5 or 10 wt %, or 0.01-10, 0.01-5, 0.01-1, 0.01-0.05, 0.1-10, 0.1-5, 0.1-1, 1-10 or 1-5 wt % of the soil composition. The effective amount of *Bacillus subtilis* UD1022 for increasing water content of the soil composition may be at least $10^5$, $10^6$, $10^7$, $10^8$ or $10^9$, or $10^5$-$10^{11}$, $10^6$-$10^{10}$ or $10^7$-$10^9$, *Bacillus subtilis* UD1022 cells per gram of the soil composition. At least 50, 60, 70, 80, 90, 95 or 99% of the *Bacillus subtilis* UD1022 cells may be viable.

The soil composition may comprise an effective amount of *Bacillus subtilis* UD1022 for reducing unsaturated hydraulic conductivity of the soil composition as compared with a control composition by, for example, as least 1, 2, 3, 4, 5, 10, 15, 20, 25, 30, 35, 40, 45, 50, 55, 60, 65, 70, 75, 80, 85, 90, 95, 99, 100 or 200%, or 1-5, 1-10, 1-20, 1-30, 1-40, 1-50, 1-60, 1-70, 1-80, 1-90, 5-10, 5-20, 5-30, 5-40, 5-50, 5-60, 5-70, 5-80, 5-90, 10-20, 10-30, 10-40, 10-50, 10-60, 10-70, 10-80, 10-90, 20-30, 20-40, 20-50, 20-60, 20-70, 20-80, 20-90, 30-40, 30-50, 30-60, 30-70, 30-80, 30-90, 40-50, 40-60, 40-70, 40-80 or 40-90%. In one embodiment, the soil composition may comprise an effective amount of *Bacillus subtilis* UD1022 for reducing unsaturated hydraulic conductivity of the soil composition as compared with a control composition by at least 5-50%. The effective amount of *Bacillus subtilis* UD1022 for reducing unsaturated hydraulic conductivity of the soil composition may be at least 0.01, 0.05, 0.1, 0.5, 1.0, 1.5, 2.0, 2.5, 3.0, 3.5, 4.0, 4.5, 5.0, 5.5 or 10 wt %, or 0.01-10, 0.01-5, 0.01-1, 0.01-0.05, 0.1-10, 0.1-5, 0.1-1, 1-10 or 1-5 wt % of the soil composition. The effective amount of *Bacillus subtilis* UD1022 for reducing unsaturated hydraulic conductivity of the soil composition may be at least $10^5$, $10^6$, $10^7$, $10^8$ or $10^9$, or $10^5$-$10^{11}$, $10^6$-$10^{10}$ or $10^7$-$10^9$ *Bacillus subtilis* UD1022 cells per gram of the soil composition. At least 50, 60, 70, 80, 90, 95 or 99% of the *Bacillus subtilis* UD1022 cells may be viable.

The soil composition may comprise an effective amount of *Bacillus subtilis* UD1022 for reducing water evaporation rate of the soil composition as compared with a control composition by, for example, as least 1, 2, 3, 4, 5, 10, 15, 20, 25, 30, 35, 40, 45, 50, 55, 60, 65, 70, 75, 80, 85, 90, 95, 99, 100 or 200%, or 1-5, 1-10, 1-20, 1-30, 1-40, 1-50, 1-60, 1-70, 1-80, 1-90, 5-10, 5-20, 5-30, 5-40, 5-50, 5-60, 5-70, 5-80, 5-90, 10-20, 10-30, 10-40, 10-50, 10-60, 10-70, 10-80, 10-90, 20-30, 20-40, 20-50, 20-60, 20-70, 20-80, 20-90, 30-40, 30-50, 30-60, 30-70, 30-80, 30-90, 40-50, 40-60, 40-70, 40-80 or 40-90%. In one embodiment, the soil composition may comprise an effective amount of *Bacillus subtilis* UD1022 for reducing water evaporation rate of the soil composition as compared with a control composition by at least 5-50%. The effective amount of *Bacillus subtilis* UD1022 for reducing water evaporation rate of the soil composition may be at least 0.01, 0.05, 0.1, 0.5, 1.0, 1.5, 2.0, 2.5, 3.0, 3.5, 4.0, 4.5, 5.0, 5.5 or 10 wt %, or 0.01-10, 0.01-5, 0.01-1, 0.01-0.05, 0.1-10, 0.1-5, 0.1-1, 1-10 or 1-5 wt % of the soil composition. The effective amount of *Bacillus subtilis* UD1022 for reducing water evaporation rate of the soil composition may be at least $10^5$, $10^6$, $10^7$, $10^8$ or $10^9$, or $10^5$-$10^{11}$, $10^6$-$10^{10}$ or $10^7$-$10^9$ *Bacillus subtilis* UD1022 cells per gram of the soil composition. At least 50, 60, 70, 80, 90, 95 or 99% of the *Bacillus subtilis* UD1022 cells may be viable.

A method for improving water content of a soil composition is also provided. The soil composition comprises soil particles. The method comprises applying *Bacillus subtilis* UD1022 to the soil composition in an amount effective for improving water retention of the soil composition.

According to the method of the present invention, the soil particles in the soil composition may constitute at least 50, 60, 70, 80, 90, 95 or 99 wt %, or 50-99, 50-90, 50-80, 50-70, 50-60, 60-99, 60-90, 60-80, 60-70, 70-99 or 70-80 wt % of the soil composition. The soil particles may have a particle size no greater than 0.05, 0.1, 0.2, 0.25, 0.3, 0.4, 0.5, 0.6, 0.7, 0.75, 0.8, 0.9, 1, 1.5 or 2 mm. The soil particles may have a particle size no less than 0.05, 0.1, 0.2, 0.25, 0.3, 0.4, 0.5, 0.6, 0.7, 0.75, 0.8, 0.9, 1, 1.5 or 2 mm. The soil particles may have a particle size in the range of 0.05-0.1, 0.05-0.25, 0.05-0.25 0.05-0.5, 0.05-1, 0.05-2, 0.1-0.25, 0.1-0.5, 0.1-1, 0.1-2, 0.25-0.5, 0.25-1.0, 0.25-2, 0.5-1, 0.5-2 or 1-2 mm.

According to the method of the present invention, at least 50, 60, 70, 80, 90, 95 or 99% of the soil particles in the soil composition may have a particle size no greater than 0.05, 0.1, 0.2, 0.25, 0.3, 0.4, 0.5, 0.6, 0.7, 0.75, 0.8, 0.9, 1, 1.5 or 2 mm. At least 50, 60, 70, 80, 90, 95 or 99% of the soil particles in the soil composition may have a particle size no less than 0.05, 0.1, 0.2, 0.25, 0.3, 0.4, 0.5, 0.6, 0.7, 0.75, 0.8, 0.9, 1, 1.5 or 2 mm. At least 50, 60, 70, 80, 90, 95 or 99% of the soil particles in the soil composition may have a particle size in the range of 0.05-0.1, 0.05-0.25, 0.05-0.25 0.05-0.5, 0.05-1, 0.05-2, 0.1-0.25, 0.1-0.5, 0.1-1, 0.1-2, 0.25-0.5, 0.25-1.0, 0.25-2, 0.5-1, 0.5-2 or 1-2 mm.

According to the method of the present invention, soil particles having a particle size no greater than 0.05, 0.1, 0.2, 0.25, 0.3, 0.4, 0.5, 0.6, 0.7, 0.75, 0.8, 0.9, 1, 1.5 or 2 mm may constitute 50, 60, 70, 80, 90, 95 or 99 wt % of the soil composition. Soil particles having a particle size no less than 0.05, 0.1, 0.2, 0.25, 0.3, 0.4, 0.5, 0.6, 0.7, 0.75, 0.8, 0.9, 1, 1.5 or 2 mm may constitute 50, 60, 70, 80, 90, 95 or 99 wt % of the soil composition. Soil particles having a particle size in the range of 0.05-0.1, 0.05-0.25, 0.05-0.25 0.05-0.5, 0.05-1, 0.05-2, 0.1-0.25, 0.1-0.5, 0.1-1, 0.1-2, 0.25-0.5, 0.25-1.0, 0.25-2, 0.5-1, 0.5-2 or 1-2 mm may constitute 50, 60, 70, 80, 90, 95 or 99 wt % of the soil composition. In one embodiment, the soil composition may comprise at least 80 wt % soil particles having a particle size no greater than 2 mm and at least 50% of such soil particles have a particle size in the range of 0.05-2 mm.

According to the method of the present invention, the soil composition may have a soil texture selected from the group consisting of sand, loamy sand, sandy loam, loam, silt loam and silt. A soil composition having a soil texture of sand may comprise about 92-100 wt % sand particles, about 0-18 wt % silt particles and about 0-10 wt % clay particles. A soil composition having a soil texture of loamy sand may comprise about 77-92 wt % sand particles, about 0-33 wt % silt particles and about 10-15 wt % clay particles. A soil composition having a soil texture of sandy loam may comprise about 50-95 wt % sand particles, about 0-53 wt % silt particles and about 15-20 wt % clay particles. A soil composition having a soil texture of loam may comprise about 40-70 wt % sand particles, about 30-53 wt % silt particles and about 7-27 wt % clay particles. A soil composition having a soil texture of silt loam may comprise about 20-55 wt % sand particles, about 55-83 wt % silt particles and about 0-27 wt % clay particles. A soil composition having a soil texture of silt may comprise about 0-25 wt % sand particles, about 85-100 wt % silt particles and about 0-10 wt % clay particles. According to the method of the present invention, *Bacillus subtilis* UD1022 may be applied to the soil composition in an amount of at least 0.01, 0.05, 0.1, 0.5, 1.0, 1.5, 2.0, 2.5, 3.0, 3.5, 4.0, 4.5, 5.0, 5.5 or 10 wt %, or 0.01-10, 0.01-5, 0.01-1, 0.01-0.05, 0.1-10, 0.1-5, 0.1-1, 1-10 or 1-5 wt % of the soil composition. *Bacillus subtilis* UD1022 may be applied to the soil composition in an amount of at least $10^5$, $10^6$, $10^7$, $10^8$ or $10^9$, or $10^5$-$10^{11}$, $10^6$-$10^{10}$ or $10^7$-$10^9$ *Bacillus subtilis* UD1022 cells per gram of the soil composition. At least 50, 60, 70, 80, 90, 95 or 99% of the *Bacillus subtilis* UD1022 cells may be viable.

According to the method of the present invention, the water retention of the soil composition may be increased by at least 1, 2, 3, 4, 5, 10, 15, 20, 25, 30, 35, 40, 45, 50, 55, 60, 65, 70, 75, 80, 85, 90, 95, 99, 100 or 200%.

The method may further comprise increasing water content of the soil composition by, for example, at least 1, 2, 3, 4, 5, 10, 15, 20, 25, 30, 35, 40, 45, 50, 55, 60, 65, 70, 75, 80, 85, 90, 95, 99, 100 or 200%, or 1-5, 1-10, 1-20, 1-30, 1-40, 1-50, 1-60, 1-70, 1-80, 1-90, 5-10, 5-20, 5-30, 5-40, 5-50, 5-60, 5-70, 5-80, 5-90, 10-20, 10-30, 10-40, 10-50, 10-60, 10-70, 10-80, 10-90, 20-30, 20-40, 20-50, 20-60, 20-70, 20-80, 20-90, 30-40, 30-50, 30-60, 30-70, 30-80, 30-90, 40-50, 40-60, 40-70, 40-80 or 40-90%. In one embodiment, the water content of the soil composition may be increased by at least 5-50%. *Bacillus subtilis* UD1022 may be applied to the soil composition in an amount of at least 0.01, 0.05, 0.1, 0.5, 1.0, 1.5, 2.0, 2.5, 3.0, 3.5, 4.0, 4.5, 5.0, 5.5 or 10 wt %, or 0.01-10, 0.01-5, 0.01-1, 0.01-0.05, 0.1-10, 0.1-5, 0.1-1, 1-10 or 1-5 wt % of the soil composition. *Bacillus subtilis* UD1022 may be applied to the soil composition in an amount of at least $10^5$, $10^6$, $10^7$, $10^8$ or $10^9$, or $10^5$-$10^{11}$, $10^6$-$10^{10}$ or $10^7$-$10^9$ *Bacillus subtilis* UD1022 cells per gram of the soil composition. At least 50, 60, 70, 80, 90, 95 or 99% of the *Bacillus subtilis* UD1022 cells may be viable.

The method may further comprise reducing unsaturated hydraulic conductivity of the soil composition by, for example, as least 1, 2, 3, 4, 5, 10, 15, 20, 25, 30, 35, 40, 45, 50, 55, 60, 65, 70, 75, 80, 85, 90, 95, 99, 100 or 200%, or 1-5, 1-10, 1-20, 1-30, 1-40, 1-50, 1-60, 1-70, 1-80, 1-90, 5-10, 5-20, 5-30, 5-40, 5-50, 5-60, 5-70, 5-80, 5-90, 10-20, 10-30, 10-40, 10-50, 10-60, 10-70, 10-80, 10-90, 20-30, 20-40, 20-50, 20-60, 20-70, 20-80, 20-90, 30-40, 30-50, 30-60, 30-70, 30-80, 30-90, 40-50, 40-60, 40-70, 40-80 or 40-90%. In one embodiment, the unsaturated hydraulic conductivity of the soil composition may be reduced by at least 5-50%. *Bacillus subtilis* UD1022 may be applied to the soil composition in an amount of at least 0.01, 0.05, 0.1, 0.5, 1.0, 1.5, 2.0, 2.5, 3.0, 3.5, 4.0, 4.5, 5.0, 5.5 or 10 wt %, or 0.01-10, 0.01-5, 0.01-1, 0.01-0.05, 0.1-10, 0.1-5, 0.1-1, 1-10 or 1-5 wt % of the soil composition. *Bacillus subtilis* UD1022 may be applied to the soil composition in an amount at least $10^5$, $10^6$, $10^7$, $10^8$ or $10^9$, or $10^5$-$10^{11}$, $10^6$-$10^{10}$ or $10^7$-$10^9$ *Bacillus subtilis* UD1022 cells per gram of the soil composition. At least 50, 60, 70, 80, 90, 95 or 99% of the *Bacillus subtilis* UD1022 cells may be viable.

The method may further comprise reducing water evaporation rate of the soil composition by, for example, as least 1, 2, 3, 4, 5, 10, 15, 20, 25, 30, 35, 40, 45, 50, 55, 60, 65, 70, 75, 80, 85, 90, 95, 99, 100 or 200%, or 1-5, 1-10, 1-20, 1-30, 1-40, 1-50, 1-60, 1-70, 1-80, 1-90, 5-10, 5-20, 5-30, 5-40, 5-50, 5-60, 5-70, 5-80, 5-90, 10-20, 10-30, 10-40, 10-50, 10-60, 10-70, 10-80, 10-90, 20-30, 20-40, 20-50, 20-60, 20-70, 20-80, 20-90, 30-40, 30-50, 30-60, 30-70, 30-80, 30-90, 40-50, 40-60, 40-70, 40-80 or 40-90%. In one embodiment, the water evaporation rate of the soil composition may be reduced by at least 5-50%. *Bacillus subtilis* UD1022 may be applied to the soil composition in amount of at least 0.01, 0.05, 0.1, 0.5, 1.0, 1.5, 2.0, 2.5, 3.0, 3.5, 4.0, 4.5, 5.0, 5.5 or 10 wt %, or 0.01-10, 0.01-5, 0.01-1, 0.01-0.05, 0.1-10, 0.1-5, 0.1-1, 1-10 or 1-5 wt % of the soil composition. *Bacillus subtilis* UD1022 may be applied to the soil composition in an amount of at least $10^5$, $10^6$, $10^7$, $10^8$ or $10^9$, or $10^5$-$10^{11}$, $10^6$-$10^{10}$ or $10^7$-$10^9$ *Bacillus subtilis* UD1022 cells per gram of the soil composition. At least 50, 60, 70, 80, 90, 95 or 99% of the *Bacillus subtilis* UD1022 cells may be viable.

Example 1. Plant Growth-Promoting Rhizobacteria (PGPR) Reduce Evaporation and Increase Soil Water Retention Enhancement of plant drought stress tolerance by plant growth promoting rhizobacteria (PGPR) has been increasingly documented in the literature. However, most studies to date have focused on PGPR-root/plant interactions; very little is known about PGPR's role in mediating physio-chemical and hydrological changes in the rhizospheric soil that may impact plant drought stress tolerance. This study aimed to advance mechanistic understanding of PGPR-mediated biophysical changes in the rhizospheric soil that may contribute to plant drought stress tolerance in addition to plant responses. Soil water retention characteristics, hydraulic conductivity, and water evaporation in soils with various textures (i.e., pure sand, sandy soil, and clay) as influenced by a representative PGPR (*Bacillus subtilis* strain UD1022) using the HYPROP system were measured. All PGPR-treated soils held more water and had reduced hydraulic conductivity and accumulative evaporation, compared to their corresponding controls. Three mechanisms, due to *B. subtilis* incubation or production of extracellular polymeric substances (EPS), that are potentially responsible for the changes in hydraulic properties and soil evaporation were discussed: (i) EPS have a large water holding capacity; (ii) EPS alter soil matrix structure and connectivity of pore space; (iii) EPS modify the physicochemical properties of water (surface tension and viscosity). These results clearly demonstrate PGPR's ability to increase water availability to plants by slowing down evaporation and by increasing the time available for plants to make metabolic adjustments to drought stress.

PGPR are a group of beneficial bacteria known to improve plant growth by, e.g., reducing pathogenic infection and/or promoting drought/salt tolerance. Despite the important role PGPR could potentially play in reducing drought stress to plants, we lack a complete understanding on the mechanisms through which PGPR mediate plant tolerance to drought. This study aimed to advance mechanistic understanding of PGPR-mediated biophysical changes in soil through microbe-soil interactions, to complement better understanding gained from previous studies that focused on microbe-plant interactions. Through laboratory measurements and imaging of water retention in soil, we show that a representative PGPR (*B. subtilis* UD1022) can increase soil water retention and reduce soil water evaporation. This effect is likely caused by the PGPR's ability to produce extracellular polymeric substances, which have high water holding capacity and can induce changes in soil physical properties. These changes lead to slower evaporation from soil, which can make more water available to plants as well as increase the time available for plants to make metabolic adjustments to drought stress. Our results provide scientific support to recent efforts in promoting application of rhizobacteria isolates as "underground resource" to contribute to solving globally-challenging issues, e.g., water resource shortage and food security.

1. Materials and Methods 1.1 Sand and Soils

To evaluate the effects of *B. subtilis* UD1022 on soil hydraulic properties and evaporation characteristics, Accusand (40/50-sieve size; Unimin Corp., Le Sueur, MN) (NIST disclaimer) or pure sand (PS), a Pepperbox (Aquic Arenic Paleudults) sandy soil (SS), and a Lenni (Typic Endoaquults) clay soil (CS) were used. The two soil samples were collected from a field experimental station located in Georgetown, DE (SS) and an agricultural farm on the University of Delaware campus (CS), respectively. The soil samples were sieved through a 2-mm sieve and air dried before use. Acid-washed pure sand and the two soil samples were autoclaved twice, at 121° C. for 15 min each time, with an intervening period of 24 h under ambient room conditions before inoculation with bacteria. Soil texture was determined using an LS™ 13 320 Series laser light-scattering particle size analyzer (Beckman Coulter, Miami, FL, USA).

1.2 Bacteria

We used *B. subtilis* UD1022 as a model PGPR in this study (Kumar, A. S., Lakshmanan, V., Caplan, J. L., Powell, D., Czymmek, K. J., Levia, D. F., & Bais, H. P. (2012). Rhizobacteria *Bacillus subtilis* restricts foliar pathogen entry through stomata. *The Plant Journal*, 72(4), 694-706). The commercial UD1022 powder is a mixture of *B. subtilis* UD1022 spores at a concentration of $2.8 \times 10^{10}$ cells/g and growth media (BASF Corp.). Using the commercially prepared *Bacillus* spores allowed uniform mixing with sand/soil samples to avoid sample heterogeneity. To address the concern of whether the other "ingredients" in the powder would have any impact on the treated samples in addition to the effects of *B. subtilis* UD1022, we included an additional treatment of *B. subtilis* UD1022 liquid culture prepared using single colonies in the neutron radiography imaging experiments on evaporation. The *B. subtilis* UD1022 liquid inoculum was prepared by growing the bacteria in Luria-Bertani (LB) broth at 37° C. for 24 h in flasks placed in a shaking water bath to a concentration of $1.3 \times 10^9$ cells/ml.

1.3 Sample Preparation

Sterilized sand/soil sample (500 g) was mixed with 1.25 g UD1022 powder and 25 g (or 50 g for clay soil samples due to its high water adsorptive capability) DI water using a kitchen blender, while corresponding control samples were mixed with the same amount of DI water without UD1022. This mixing ratio gave a consistent initial concentration of $7 \times 10^7$ cells/g for the different textured soils. The *B. subtilis* UD1022 were grown overnight, the culture was subsequently centrifuged and the pellet was washed with DI water. A bacteria suspension was further diluted and mixed with soil samples at the same bacterial concentration ($7 \times 10^7$ cells/g). The sand/soil samples were stored under ambient room conditions for 24 h before conducting the HYPROP experiments or neutron radiography imaging.

1.4 Determination of Hydraulic Properties

We used the commercial HYPROP system (UMS, Munich, Germany) to measure hydraulic properties of the 3 soils treated with UD1022 and their controls. HYPROP determines the soil water retention curve (WRC) and the hydraulic conductivity curve (HCC) using a simplified evaporation method (Peters, A., & Durner, W. (2008). A simple model for describing hydraulic conductivity in unsaturated porous media accounting for film and capillary flow. *Water Resources Research*, 44(11); Peters, A., Iden, S. C., & Durner, W. (2015). Revisiting the simplified evaporation method: Identification of hydraulic functions considering vapor, film and corner flow. Journal of Hydrology, 527, 531-542). To initiate measurement, each treated or control soil sample was first packed into a HYPROP sample ring (volume=249 cm³, height=5 cm) following a standardized procedure (Klute, A., & Dirksen, C. (1986). Hydraulic conductivity and diffusivity: Laboratory methods. *Methods of soil analysis: part 1-physical and mineralogical methods*, (methodsofsoilan1), 687-734). The packed soil cores were saturated from bottom to top by partially immersing them in DI water overnight. A pair of fully saturated samples (treated and control), which were mounted onto the HYPROP measuring heads with two tensiometers installed at different depths in each sample, was run for each soil. The experiments were conducted in a closed environmental chamber, which was slightly heated using a heating pad. A temperature controller was used to maintain a constant temperature of 25° C., which was higher than the ambient room temperature in the laboratory to increase evaporation rate thus shortening the experiment. A dehumidifier was placed in the chamber to avoid excessive humidity due to the continuous evaporation in the closed chamber.

The saturated soil samples were allowed to evaporate while the HYPROP system continuously monitored the weight of each sample and matric potentials at two depths. In this manner, soil water content was calculated from changing soil mass whereas a corresponding soil matric potential value was averaged from the tensiometer readings at the two depths at any given time. Unsaturated hydraulic conductivity was then calculated by relating the gradient in matric potential to water flux (soil mass change) using the Darcy-Buckingham law. This simplified evaporation method was considerably less time consuming compared to traditional methods, e.g., the pressure plate or the hanging water column method; and it did not require complex numerical computations as used in inverse parameter fitting (Šimůnek, J., van Genuchten, M. T., & Wendroth, O. (1998). Parameter estimation analysis of the evaporation method for determining soil hydraulic properties. *Soil Science Society of America Journal*, 62(4), 894-905). In addition, this method provides quantitative information on evaporation, and thus allows examination of the effects of *B. subtilis* UD1022 on evaporation processes as well.

Each experiment was terminated after the tensiometer readings reached the bubbling pressure. The soil sample was then oven-dried at 105° C. for 24 h and weighed for final water content calculation. Two or three replicate experiments were conducted for each soil type.

1.5 Soil Particle Imaging

To verify the existence of EPS on the surface of soil particles, microscopic images of dry pure sand samples post UD1022-treatment were taken using SEM (Hitachi, S-4700, Japan) and an optical microscope (Olympus 3Max, Japan). At the end of the HYPROP measurements, ~1 g soil was sampled from each treatment and dried at ambient room conditions for 24 h. The samples were attached onto a piece of carbon tape for SEM visualization. In a separate experiment, we used a light transmission microscope to image the spatial distribution of EPS on sand particles, which were incubated with UD1022 and fully saturated with DI water in a petri dish. After drying under ambient room conditions, the petri dish was placed under an optical microscope for visualization.

1.6 Neutron Radiography

Neutron radiography, a powerful imaging technique for water due to the strong attenuation by hydrogen in water, was used to visualize in situ water distribution and variance in soil cores during evaporation as affected by UD1022. Imaging was performed at the National Institute of Standards and Technology (NIST) Center for Neutron Research (NCNR) BT-2 imaging beam line. The detector used for this study was an Andor NEO scientific complementary metal oxide semiconductor (sCMOS) camera that views a gadolinium oxysulfide scintillator (Lexel Imaging P-43 phosphor). Custom-made soil columns (Ø1.0 cm×2.5 cm) were packed with control and incubated sandy soil samples with powder- and liquid-cultured bacteria, and saturated in a water bath from bottom to top. The three saturated soil columns were placed in a row and exposed to the neutron beam for radiography. All samples were imaged simultaneously to ensure the same environmental conditions. The field of view was 6.4 cm by 7.6 cm, with a resolution of 60 µm. Exposure time of 22 s yielded an optimal grayscale range in the radiograph. A total of 1500 individual images were acquired continuously over a 9.2 h period as the samples dried. Sets of three consecutive images are median combined to reduce random noise and the combined image has a 3 by 3 median spatial filter applied to remove shot noise. The purpose of conducting neutron radiography imaging were two-fold: 1) to provide direct visual evidence of UD1022's effect on evaporation and 2) to test whether the "ingredients" in the UD1022 powder would impact the treated samples in addition to the bacteria by comparing with a liquid *B. subtilis* UD1022 culture.

2. Results 2.1 Water Retention Curve (WRC)

FIGS. 2*a-c* show the measured WRCs for UD1022-treated and control soil samples, which reveal a general increase in water retention in response to UD1022 treatment. The saturated water content of each UD1022-treated sample was consistently greater than its control (Table 1).

effect on natural soils (SS and CS) was less obvious (FIG. 2*a*), i.e., ~−25 cm for both treatments of SS, and −50 cm for both treatments of CS.

We fitted the van Genuchten-Mualem (VGM) model to the measured water retention curves (FIG. 2*d-f*). The VGM model is expressed as, $$\theta = \theta_r + \frac{\theta_s - \theta_r}{[1 + (\alpha|\psi|)^n]^{1-1/n}}, \quad (1)$$

where $\theta$ and $\psi$ are water content (cm$^3$ cm$^{-3}$) and matric potential (cm of water); $\theta_s$ and $\theta_r$ are saturated and residual water content (cm$^3$ cm$^{-3}$), respectively; a is related to the inverse of the air entry value (cm$^{-1}$), and n is α measure of pore size distribution. The fitted parameters θr, n, and α are listed in Table 1. Greater $\theta_r$ and smaller n values were obtained for UD1022-treated samples than the controls. Greater α values were found for UD1022-treated pure sand than its control, while α values were not significantly different between treatments for sandy soil and clay. The goodness of the model fitting was quantified by the root mean square error (RMSE), as listed in Table 1. The RMSE values were much smaller than the saturated or residual water contents for all three types of soils, indicating the model fitted the experimental data considerably well.

2.2 Unsaturated Hydraulic Conductivity $K_r$

The unsaturated hydraulic conductivity ($K_r$) values are shown as a function of water content (FIGS. 3*a-c*) or matric potential (FIGS. 3*d-f*), respectively. The $K_r$ values of all control samples were consistently and significantly larger than the values of the UD1022-treated samples at any given water content. Plots as a function of matric potential (FIG. 3*d-f*) show that the $K_r$ values for the UD1022-treated pure sand and sandy soil were reduced compared to the controls, but they approached the conductivity values of their controls at the drier measuring limits. However, the difference in $K_r$ values between the two treatments of clay was less obvious and even shows a slightly opposite trend, i.e., a greater $K_r$ value for the UD1022-treated clay than for the control at the drier end of the curve.

TABLE 1

Physical Properties of Tested Soil Samples: Particle Size Fraction, Porosity, Water Retention Curve Parameters using VGM, and Calculated Evaporation Characteristic Length

|  |  | Pure sand (PS) | Sandy soil (SS) | Clay soil (CS) |
|---|---|---|---|---|
| Particle size fraction (%) | <0.002 mm | 0.297 mm-0.420 mm | 1.4 | 67.3 |
|  | <0.05 mm |  | 9.4 | 20.6 |
|  | <2 mm |  | 89.2 | 12.1 |

|  |  | PS-C | PS-T | SS-C | SS-T | CS-C | CS-T |
|---|---|---|---|---|---|---|---|
| Porosity (%) |  | 37.7 ± 1.9 | 37.3 ± 1.5 | 40.7 ± 2.8 | 41.8 ± 2.4 | 47.9 ± 0.7 | 47.9 ± 0.4 |
| $\theta_s$ (Vol %) |  | 35.8 | 38.1 | 41.0 | 41.5 | 47.8 | 53.7 |
| VGM parameters | $\theta_r$ (Vol %) | 5.9 | 8.8 | 16.0 | 22.2 | 8.9 | 11.6 |
|  | n | 9.07 | 5.96 | 2.94 | 2.81 | 1.63 | 1.18 |
|  | a (cm$^{-1}$) | 0.052 | 0.108 | 0.023 | 0.025 | 0.016 | 0.015 |
| RMSE for VGM fitting Vol %) |  | 0.66 | 0.79 | 1.24 | 1.38 | 0.51 | 0.27 |
| $L_G$ (cm) |  | 7.2 | 4.9 | 34.2 | 32.0 | 113.6 | 333.4 |
| $e_0$ (cm/d) |  | 0.210 | 0.184 | 0.149 | 0.137 | 0.205 | 0.184 |
| $k_{eff}$ (cm/d) |  | 0.095 | 0.089 | 0.019 | 0.007 | — | — |
| $L_C$ (cm) |  | 2.2 | 1.6 | 3.8 | 1.6 | — | — |

UD1022 treatment had more pronounced effect on the drier end of WRCs (between −10$^3$ cm and −10$^2$ cm) for all samples. The addition of UD1022 increased water content (averaged by 2 replicates) by 9.2%, 5.8%, and 11.7% in pure sand, sandy soil, and clay, respectively, within the tension range up to −10$^3$ cm, while at the drier end (e.g., >−10$^3$ cm), the effects of UD1022 was greater, increasing the water content of sandy soil and clay by 55.4% and 92.8%, respectively. Water content in UD1022-treated pure sand increased by 69.7% compared with the control at matric potential of −5×10$^2$ cm. Another observation on changes in WRC in response to UD1022 treatment was that UD1022-treated pure sand had a lower (i.e., less negative) bubbling-pressure value, i.e., −13.7 cm for the control and −7.5 cm for the treated sample, when water in large pores drained and only a small amount of water remained, than the control. Such

2.3 Evaporation

Measurements by HYPROP. Cumulative water evaporation measured with HYPROP for all samples is plotted in FIG. 4. Consistently, less water was lost due to evaporation from UD1022-treated soils than from the controls, under the same controlled atmospheric conditions (temperature and moisture), during the first 5 (pure sand), 10 days (clay), and after 10 days (sandy soil) of evaporation. After 10 days, the cumulative water loss from the UD1022-treated pure sand approached a similar value to its control treatment, the difference between the two treatments of sandy soil widened, and the cumulative water loss from UD1022-treated clay soil surpassed its control.

Figure 4:
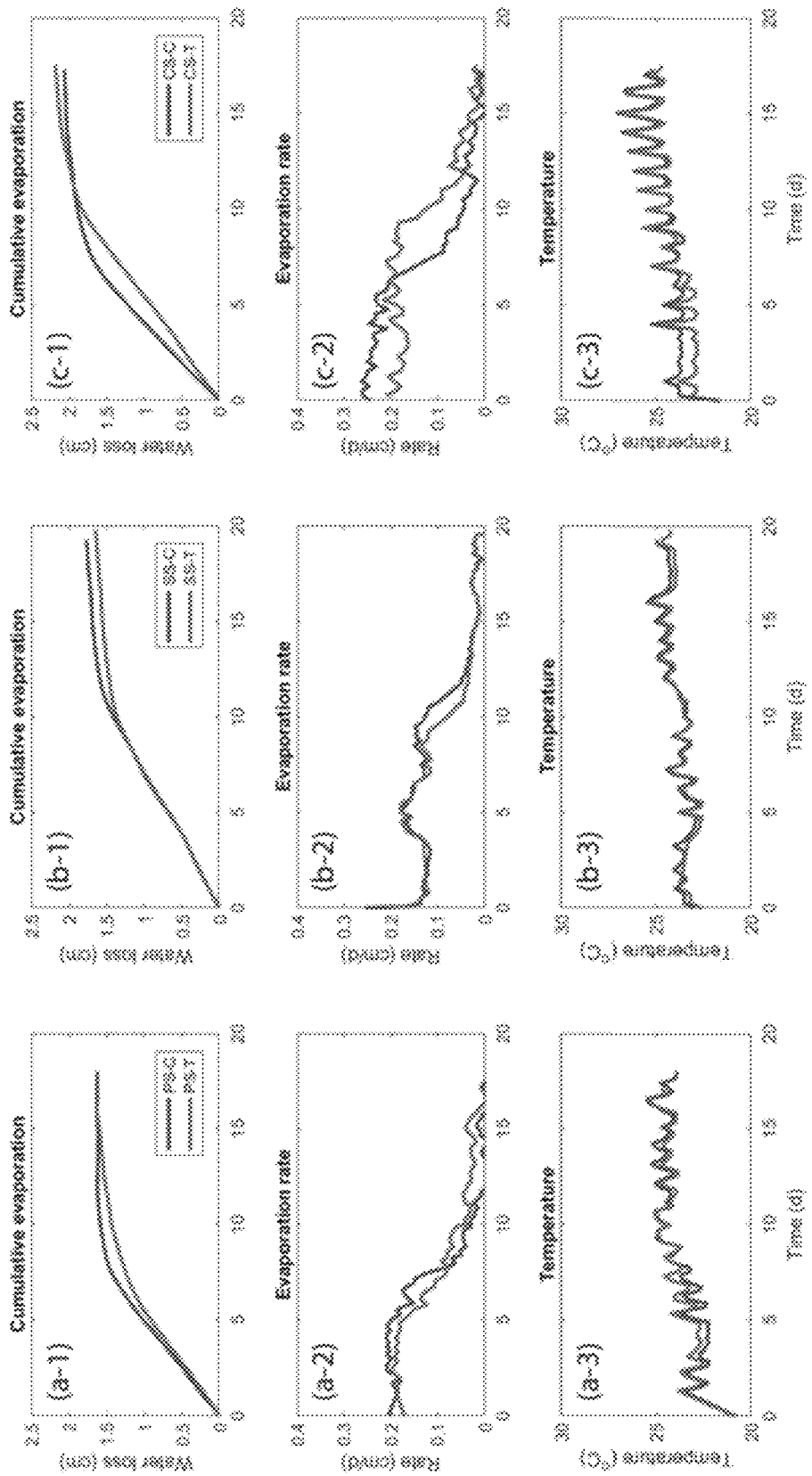
FIG. 4 shows cumulative evaporation (1), evaporation rate (2), and soil water temperature (3) measured with HYPROP for UD1022-treated (T) and control (C) soil samples: (a) pure sand: PS; (b) sandy soil: SS; (c) clay: C.

FIG. 4 also shows water evaporation rates as a function of time for the different soils. First, all evaporation rate profiles exhibited the 2-stage evaporation characteristics, i.e., Stage I with an initially high and relatively constant evaporation rate and Stage II with a lower and gradually reducing evaporation rate. Second, the length of Stage I varied between control and treated samples for all the soils. For the coarser-textured sand/soil (PS and SS), Stage I evaporation lasted longer for controls than the UD1022-treated samples. The trend was reversed in the clay samples, i.e., Stage I lasted longer but with a lower rate for the UD1022-treated samples than the controls. Also plotted are temperature profiles showing measurements of temperature of soil inside of the HYPROP rings.

Figure 5:
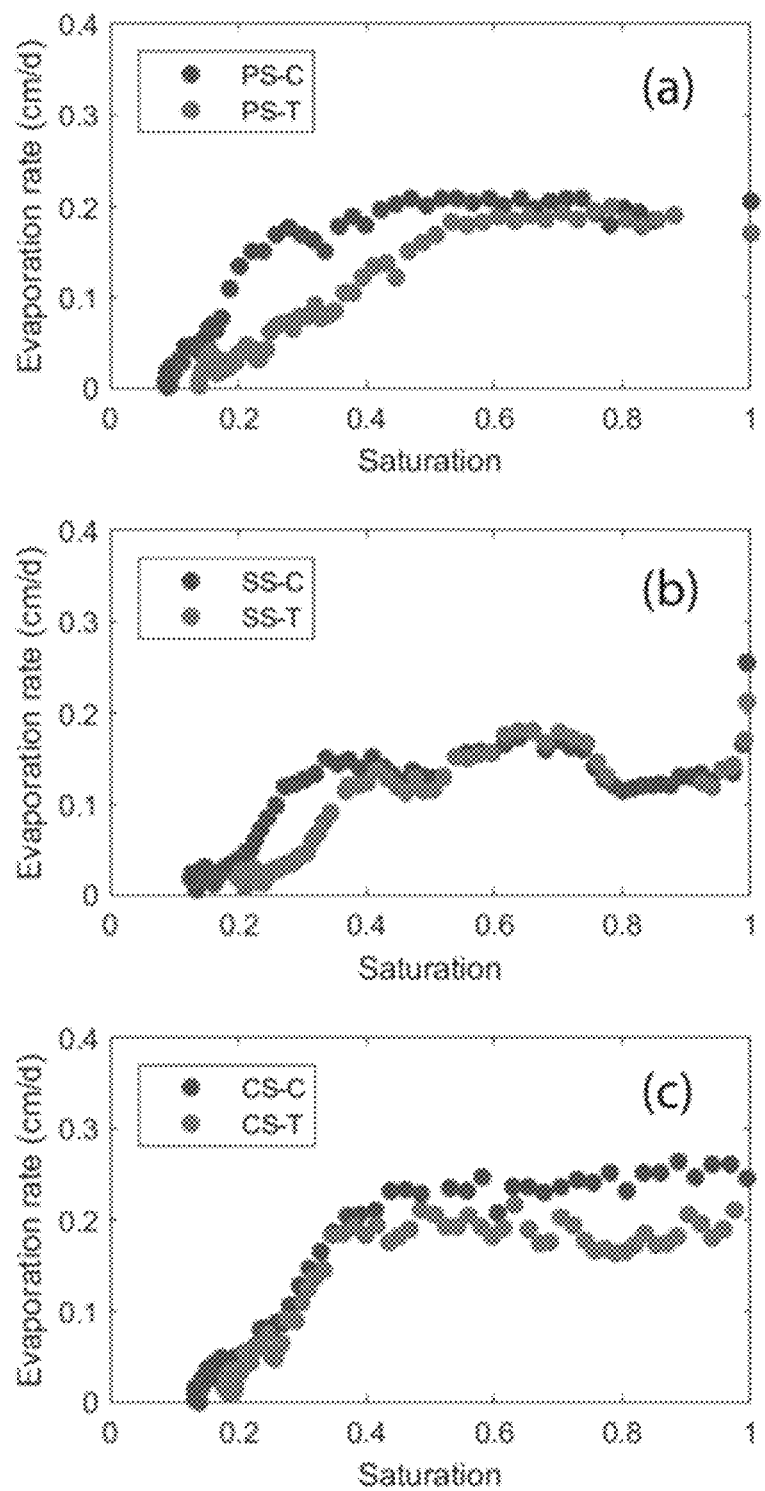
FIG. 5 shows evaporation rate as a function of water saturation for UD1022-treated (T) and control (C) soil samples: (a) pure sand: PS; (b) sandy soil: SS; (c) clay: CS.

Evaporation rate is plotted as a function of water saturation in FIG. 5. The evaporation rate vs. saturation curves also exhibited the 2-stage evaporation characteristics, i.e., Stage I with a relatively constant rate at high degrees of saturation, and Stage II with a rapidly decreasing rate at lower degrees of saturation. However, the shapes of these curves were different for different textured soils. For example, the evaporation rates from coarse-textured PS and SS samples were similar between treated and control samples at high saturation but the values for the UD1022-treated samples were much lower than the controls at lower saturation. In addition, the decrease in evaporation rate began at higher saturation for treated samples. To the contrary, the control clay sample had higher evaporation rates than UD1022-treated during Stage I at high saturation but slightly lower rates at low saturation. Our replicate experiments illustrate consistent qualitative observations, but quantitatively, there was difference between replicates, such as the absolute value of evaporation rate, the duration of Stage I, due to different external environmental conditions.

Visualization by Neutron Radiography. The evaporation process of UD1022-treated and control sandy soil samples were imaged using neutron radiography; the dry-out progression was observed. The UD1022-treated soil samples consistently dried more slowly than the control, which agreed well with the evaporation data from the HYPROP experiments. The drying-out profiles of the powder-form bacteria and the liquid-cultured bacteria were comparable. The profiles of all the soil samples elucidate the heterogeneous characteristic of water distribution during evaporation. This could be due to nonuniform packing.

3. Discussions

Figure 6:
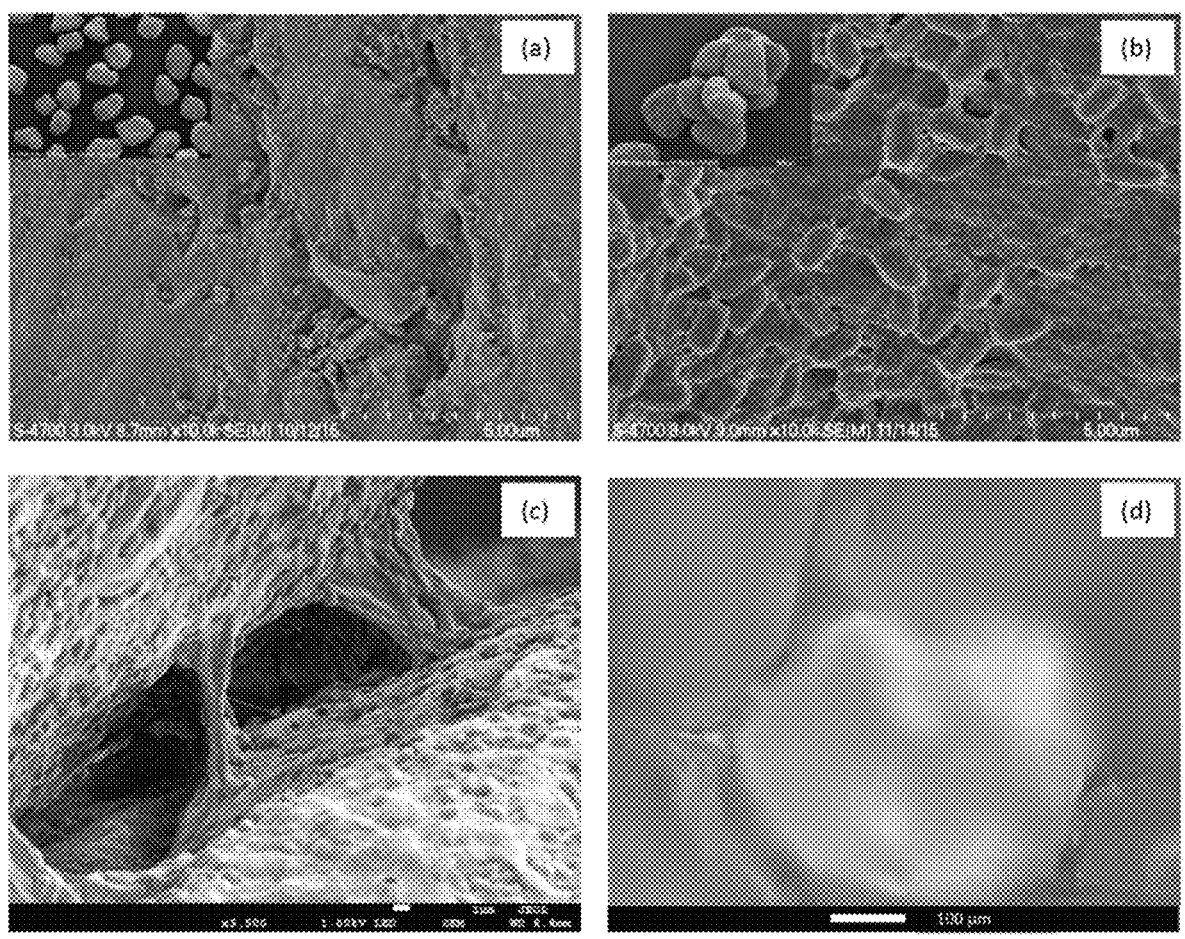
FIG. 6 shows microscopic images of pure sand samples without (a) and with (b, c, and d) UD1022 incubation.

Through measurements using the HYPROP system, we demonstrated that UD1022 treatment increased soil water retention and reduced unsaturated hydraulic conductivity and evaporation. In addition, we showed, both quantitatively (the HYPROP measurements) and through direct visualization (neutron radiography imaging), that UD1022 also reduced water evaporation from treated soil samples. To gain understanding on the mechanisms of how UD1022 mediated the changes in treated soil samples that led to the increase in water retention and decrease in hydraulic conductivity and evaporation, we performed imaging with SEM and light microscope of sand particles from treated and control samples (FIG. 6). FIG. 6a shows the control sand particles with clean surfaces whereas FIG. 6b shows rod-shaped bacteria cells distributed in a continuous and thick layer of dried biofilm covering UD1022-treated sand particles. It should be noted that the SEM images were taken with air-dried particles thus dehydration might have altered the native 3D biofilm structure. Biofilm was observed on a polystyrene substrate under hydrated and dehydrated conditions using Environmental SEM. Bacterial cells of *B. subtilis* were embedded in mucoid-like structures in hydrated matrix, and upon gradual dehydration, the cells were connected by a dense and oriented network of fibers, similar to the structures shown in FIGS. 6b and 6c. The mucus material under hydrated condition and the fibrous skeleton under dehydrated conditions were also observed, and was identified as EPS. Therefore, it is reasonable to conclude that UD1022 produced EPS and formed biofilm in the treated soil samples.

EPS/biofilm caused aggregation of sand particles post UD1022-treatment, while no aggregation was observed in the control sample (image inserts in FIGS. 6a and 6b); dried biofilm formed a skeleton-like structure and created hollow spaces in between sand particles (FIG. 6c). Biofilm was also found between sand particles, especially in the small pores (FIG. 6d).

Increased soil water retention has also been observed in soil treated with other EPS-producing bacteria strains, e.g., *Pseudomonas*, in soil samples mixed with extracted EPS or root/seed mucilage, or EPS analogues such as dextran, xanthan, scleroglucan. Reduced saturated conductivity was observed in sand columns inoculated with EPS-producing bacteria strain. A reduction was reported in both saturated and unsaturated hydraulic conductivity in soil samples after incubation with *Pseudomonas*. Dried mucilage were observed deposited in between glass beads formed bridges or filaments depending on mucilage concentration.

Mathematical models have been developed to take into account the effects of EPS or mucilage on soil water retention and hydraulic conductivity. For example, a composite model was proposed to treat soil phase and EPS as two separate media and water content or hydraulic conductivity was computed at any given potential as a linear superposition of that in each phase. This approach was applied to compare with measured water retention data and it was concluded that the dominant mechanism for increased water retention was EPS' distinct water holding capacity. A different approach was to assume that mucilage occupies small pores and creates additional potential during drying, so that water retention increases, especially under dry conditions. In a more complex model, EPS was treated as a separate phase and considered their swelling properties in addition to soil pore size change due to EPS treatment. All the modeling results indicate a small amount of EPS or mucilage could lead to significant changes in water retention and hydraulic properties.

Based on the above analysis, we propose three mechanisms that are potentially responsible for the observed UD1022 effects on soil hydraulic properties: (i) EPS have large water holding capacity; (ii) EPS alter soil structure and connectivity of the pore space; (iii) EPS modify the wettability of soils surfaces. These mechanisms are discussed in more detail below.

Large water holding capacity of EPS. A common structural feature of bacterial EPS, plant mucilage, or EPS analogues is the complex 3D network composed of polymeric strands, bonded by electrostatic interactions, hydrogen bonds, and London dispersion forces. The cross-linked and compact EPS matrix behaves like a sponge, and is capable of absorbing water at an amount of tens (xanthan or pure bacterial EPS) or hundreds (root mucilage of maize) of times of its dry weight. Experimental studies showed that pure xanthan held 50 to 70 g of water per g of xanthan while maintaining structural coherence. It has been reported that EPS are hygroscopic and can retain water entropically rather than through specific water binding mechanisms. Water absorption can result in swelling of EPS matrix leading to progressive increase in spaces between their biopolymetric strands. This effect may be partially responsible for the observed increase in water retention at high saturation levels in UD1022-treated samples compared to their controls. As shown in Table 1, the initial water content in UD1022-treated samples was consistently higher than the controls despite the fact that they had similar porosities.

Figure 3:
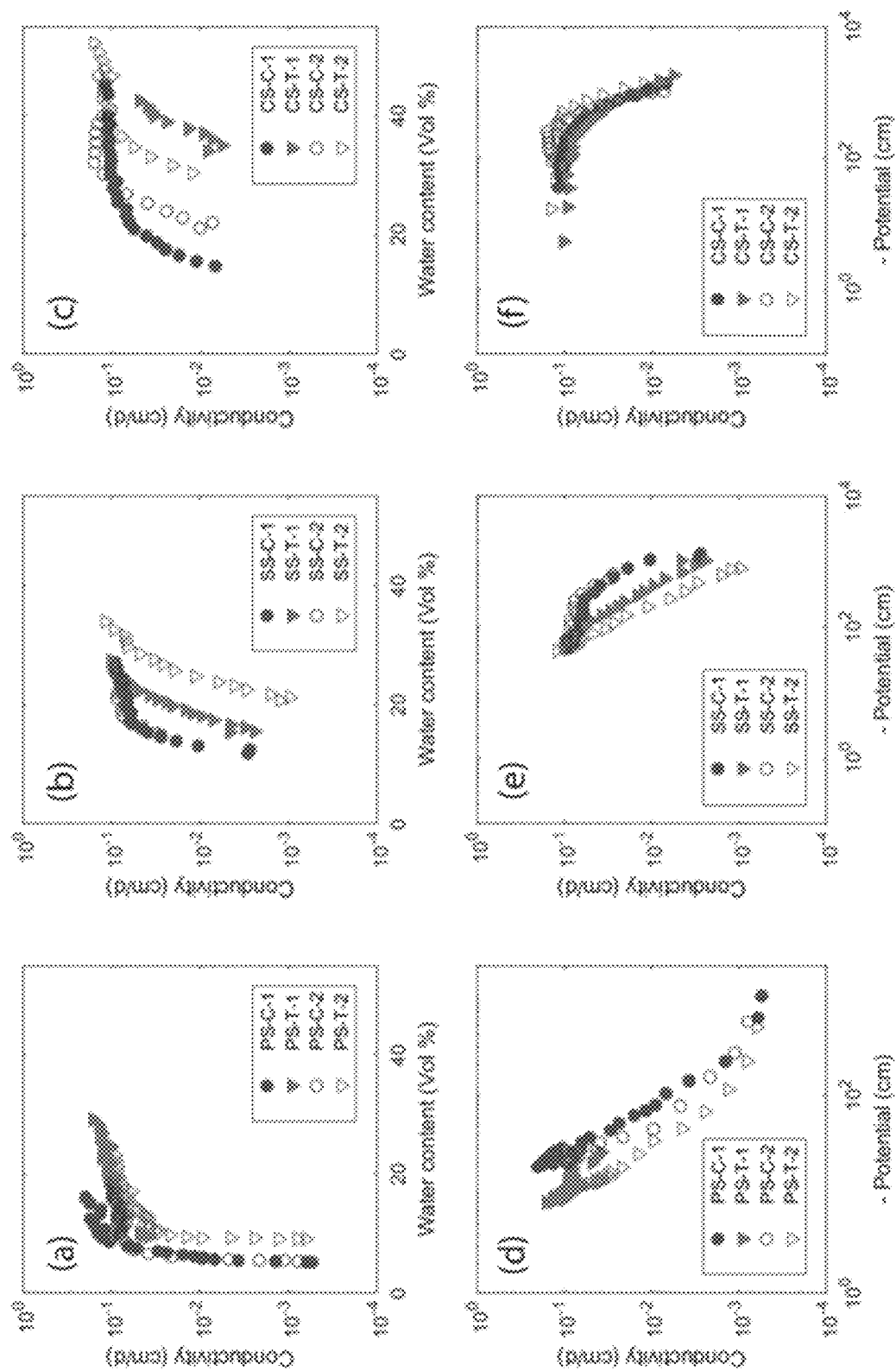
FIG. 3 shows hydraulic conductivity versus soil water content (a-c) and water potential (d-f) for UD1022-treated (T) and control (C) soil samples (pure sand: PS; sandy soil: SS; clay: CS).

The large water holding capacity of EPS was regarded as the dominant mechanism for the modified water retention upon EPS amendment. However, water holding capacity of pure EPS decreases dramatically with decreasing matric potential. It was showed that, for 3 types of EPS analogs, while water content decreased continuously with decreasing matric potential, the most significant decrease (by ~⅔) occurred at potential between −10 cm to −$10^3$ cm, suggesting that the high water holding capacity of EPS has less significant effect as the soil sample became drier. However, our results show that UD1022 had more pronounced effects at more negative matric potential (between −$10^2$ cm and −$10^3$ cm), drier conditions in all samples tested (FIG. 3). It has also been reported significant increase in soil water content post bacterial incubation occurred at the matric potentials more negative than −60 cm. Consistently, more pronounced increased in water content has been found at the drier end. In addition, soils with different textures responded to EPS or mucilage treatment differently, indicating that other mechanisms might have also played a role in increasing soil water retention.

Modification in soil pore structure. EPS-induced particle aggregation resulted in modification of soil pore size distribution (FIG. 6b), which is reflected by the fitted VGM parameter n (Table 1), where a smaller n value corresponds to a narrower pore size distribution. This can be due to clogging of small pores by EPS or EPS filaments connecting large pores into smaller spaces or formation of porous network, as shown in FIGS. 6c and 6d and as previously reported. The newly created smaller pore spaces can lead to additional water retention due to increased capillarity. Calculations of potential vs. water saturation have been presented, based on a pair of spheres affected by maize mucilage, and demonstrated that capillary bridging could lower water potential by orders of magnitude in the presence of mucilage compared to a system with pure water.

Figure 2:
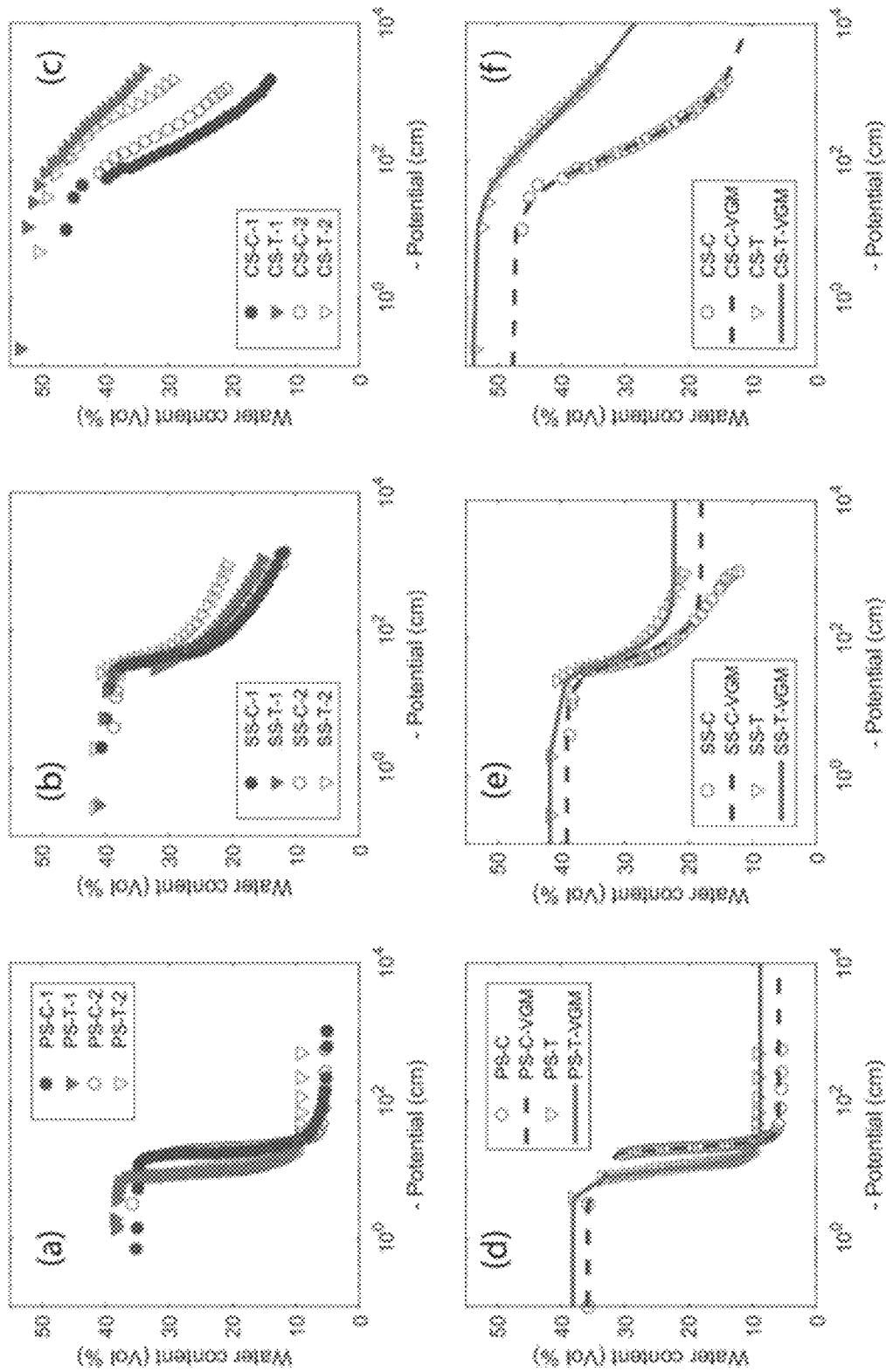
FIG. 2 shows soil water retention curve of UD1022-treated (T) and control (C) soil samples (pure sand: PS; sandy soil: SS; clay: CS) measure by HYPROP. (a)-(c) show two replicate measurements (1 and 2) for each soil and (d)-(f) show one set of measurements and fitted results using VGM model.

In addition to capillarity dominated water retention, water is also adsorbed as thin films by van der Waals forces. Water film thickness has been used to estimate the dry end of water retention curve, assuming that capillary contributions become negligible for matric potential values lower than −100 hPa. Water content was consistently higher in UD1022-treated samples than in the controls at the dry region of the measured water retention curves (FIG. 2). Given the relationship between water content θ and specific surface area $s_a$, $\theta = h \times s_a \times \rho_w$, where h is film thickness (m), and $\rho_w$ is water density (kg m$^{-3}$), the increased water content post UD1022 treatment (thus with the presence of bacteria colonies or EPS) could be due to increase of surface area or film thickness or both. First, upon dehydration, filament network formed by EPS in between soil particles could create additional surface area. Second, bacteria colonies could increase surface roughness thus increasing the surface area of treated sand particles. Lastly and more importantly, it has been shown that surface roughness increases water film thickness. It has been reported that measured effective water film was ~2 orders of magnitude thicker on a rock surface at intermediate to low suction region (−10 cm to −$10^2$ cm) compared with results calculated assuming a smooth surface. In view of surface roughness in calculations using water retention data from several natural soils, it was demonstrated that the effective water film thickness values were significantly greater than the theoretical values previously reported. Capillary condensation and adhesion of two wetter surfaces. Therefore, all three mechanisms discussed above could have collectively affected water retention induced by UD1022 treatment, although the relative significance of each individual contribution is difficult to distinguish without additional study.

Wettability and viscosity. Surface wettability and surface tension of a water-air interface determine the work needed to drain or absorb water upon changing matric potential. A simple sand medium (e.g., sand control without UD1022 treatment) contains a water phase and particles that are largely hydrophilic whereas natural soils usually are less hydrophilic due to the presence of hydrophobic organic matter. EPS add additional complexity to the phases in UD1022-treated soil samples. It was found that EPS reduced surface tension, which they attributed mainly to the presence of phospholipids in the EPS. In addition, mature biofilms tend to display persistent resistance to liquid wetting, therefore, EPS can increase the hydrophobicity of soil particles.

The physicochemical properties of biofilms (i.e., lower surface tension or greater hydrophobicity) generally decrease soil water retention. On the one hand, the capillary pressure $h_{cap}$ needed to drain a cylindrical pore is determined by the surface tension of the fluid-air interface a and the contact angle between the liquid phase and particle surface β, according to the Young-Laplace equation, $h_{cap} = -\sigma \cos \beta / r$, where r is the pore radii (m). Presence of biofilm, which leads to a smaller σ and smaller cos β, implies less work is needed to drain a pore. On the other hand, lower surface tension decreases the amount of water that can be retained in pore corners, assuming soils pores are angular. This is because the radius of curvature of the liquid-gas interface associated with the water retained in pore corners, determined by the Young-Laplace equation, decreases with reducing surface tension.

While both mechanisms influence water retention characteristics, their relative contribution is determined by soil texture and degree of saturation. Clay has a broader pore size distribution and more irregular particle/pore shapes than pure sand or sandy soil, and thus the shape of water retention curve of clay is more significantly influenced than coarser textured soils (FIG. 2). However, drainage of water in large pores can occur earlier (e.g., at a lower bubbling pressure) in UD1022-treated samples at lower surface tension with the presence of EPS, which explains the difference in water retention curve between the treatments in pure sand (FIG. 2a).

Composed of polymeric substances, EPS generally exhibit larger viscosity compared to water thus increase flow resistance. It was reported that the viscous biofilm produced by Strain 3610 *B. subtilis* cells measured at an air-liquid interface was 200 times higher than pure water. Therefore, in the presence of EPS, the pore-scale flow conductance can be largely reduced as it is inversely proportional to viscosity leading to less mobile water. This provides another mechanism for the reduced hydraulic conductivity observed in the UD1022-treated soil samples, in addition to pore clogging.

Overall, the effect of EPS on water retention and hydraulic conductivity is two-fold: while the retained water is less mobile (i.e., reduced conductivity) due to higher viscosity, there are more saturated soil pores at the same potential due to reduced surface tension. Our study, for the first time, provides the direct experimental evidence that biofilm enrichment could increase unsaturated hydraulic conductivity in fine-textured media.

Link soil hydraulic properties to evaporation characteristics. Evaporation measured by the HYPROP system and neutron imaging provides convincing evidence on UD1022's ability to increase soil water retention by reducing hydraulic conductivity and rate of evaporation in all soil samples. Evaporation retardation upon bacteria treatment was reported. Another observation is that all evaporation rate profiles exhibit the 2-stage evaporation characteristics. The mechanisms controlling the transition from Stage I to Stage II evaporation have been previously discussed. The constant evaporation rate during Stage I is maintained due to continuous capillary flow between the evaporation surface and the drying front, which is the boundary separating water-saturated and partially-unsaturated zones. Breakage of liquid connections leads to a rapid drop in evaporation rates, marking the end of Stage I. The distinct evaporation rates at the two stages are the results of different mechanisms that control the two distinct periods and the transition from Stage I to Stage II, which in turn is affected by soil properties.

Theoretically, the transition from Stage I to Stage II is a result of the interplay among capillarity, gravity, and viscous forces. The relative importance between the different forces (i.e., gravitational and capillary forces or viscous and capillary forces) is characterized by the Bond number $$\left(Bo, Bo = \frac{\rho g}{\sigma} r^2\right)$$

and capillary number $$\left(Ca, Ca = \frac{\eta e_0}{\sigma} \frac{r^2}{\kappa}\right),$$

respectively, with r being the characteristic pore size (m), $\rho$ the water density (kg m$^{-3}$), g the acceleration due to gravity (N kg$^{-1}$), $\sigma$ the surface tension (N m$^{-1}$), $\eta$ the dynamic viscosity (Pa s), $e_0$ the drying rate (cm/d), and $\kappa$ the permeability, which is related to hydraulic conductivity $K_r$ as $$\kappa = \frac{K_r \eta}{\rho g}.$$

More quantitatively, the characteristic length of phase continuity, which describes the maximum drying front depth for the end of Stage I, can be used to characterize the evaporation process (Lehmann, P., Assouline, S., & Or, D. (2008). Characteristic lengths affecting evaporative drying of porous media. Physical Review E, 77(5), 056309). The characteristic length of phase continuity $L_c$ is written as:

$$L_C = \frac{L_G}{1 + \frac{e_0}{K_{eff}}} \quad (2)$$

where, $K_{eff}$ is the unsaturated hydraulic conductivity above the drying front (cm/d), and $L_G$ is the gravitational characteristic length (cm). Relating $L_G$ to pore size distribution using the VGM model, $L_G$ is expressed as, $$L_G = \frac{1}{\alpha(n-1)} \left(\frac{2n-1}{n}\right)^{\frac{2n-1}{n}} \left(\frac{n-1}{n}\right)^{\frac{n-1}{n}} \quad (3)$$

The previously discussed three mechanisms (large water holding capacity, lower surface tension and larger viscosity of EPS, and related soil pore structural changes) that are potentially responsible for the observed changes in soil hydraulic properties due to UD1022 treatment can also affect soil evaporation transition from Stage I to Stage II. Firstly, as EPS are hygroscopic, it may lead to different drying curves compared with non-hygroscopic material (e.g., sand and soil) because a constant evaporation rate generally does not exist for hygroscopic materials. Thus, hygroscopy may be responsible for the more gradual transition from Stage I to Stage II for UD1022-treated pure sand compared with the control. This effect is less obvious in the sandy and clay soils, which have larger specific surface areas to adsorb EPS to prevent it from being a separate phase to exhibit hygroscopic properties.

Secondly, as EPS decreases surface tension and increases viscosity, both the Bo and Ca values would increase post UD1022 treatment, indicating that capillary force played a less dominant role over gravity and viscosity in controlling the flow behavior. Therefore, EPS presence can facilitate the end of Stage I. Indeed, the durations of Stage I for UD1022-treated pure sand and sandy soil were shorter than for their controls.

Thirdly, the characteristic length implicitly considers pore structural changes in addition to surface tension and viscosity. The $L_G$, $K_{eff}$, $e_0$, and $L_C$ values calculated for all soil samples are listed in Table 1. The unsaturated conductivity ($K_{eff}$) and evaporation rate ($e_0$) values were determined by firstly identifying the transition point on the evaporation rate curve. The characteristic lengths $L_G$ and $L_C$ for the UD1022-treated pure sand and sandy soil were shorter than their respective controls, indicating shorter durations of Stage I evaporation. Although the calculated $L_G$ was greater for UD1022-treated clay, this trend is not necessarily true for $L_C$, as the unsaturated hydraulic conductivity was also reduced for the UD1022-treated sample.

Finally, it should be noted that the $K_{eff}$ values for clay could not be estimated because the transition of evaporation occurred at the matric potential that exceeded the measurement range. It may indicate that the evaporation characteristic length is longer than the column length. In this case, it is inappropriate to correlate the calculated characteristic length to the measured duration of Stage I, as termination of Stage I is caused by the limited column length, rather than the physical properties of soil.

4. Conclusions and Practical Implications

Using as a model PGPR, we studied the effects of *B. subtilis* UD1022 (UD1022) on soil hydraulic properties and evaporation for different textured soils, including a pure sand, a sandy soil, and a clay soil. Due to *B. subtilis* UD1022's ability to produce EPS, UD1022-treated soil samples retained more water, had reduced unsaturated hydraulic conductivity and lower water evaporation rate compared to the controls. Our analyses indicate that EPS mediate changes in soil water-holding capacity and evaporation characteristics via three potential mechanisms: (1) the hygroscopic EPS can retain large quantities of water, (2) EPS modify soil pore-size distribution, and (3) EPS modify soil water properties (i.e., decrease surface tension and increase viscosity). While we do not have direct proof on the contribution of EPS' hygroscopic property to the observed results, we provide clear evidence, both visually and through modeling, on changes of soil structure and pore-size distribution in treated soil samples. Additionally, we demonstrate how EPS can increase water retention and reduce evaporation through changes in surface tension and viscosity. Improved understanding and further detangling of the mechanisms involved may be obtained through well-designed pore-scale experimental and theoretical work.

The increased water retention and decelerated evaporation point to the potential effectiveness of using PGPR to help relieve the stress plants experience during drought. Under drought conditions, the very limited amount of water is likely to cause hydraulic failures either because roots shrink or the soil's conductivity cannot sustain the transpiration demand. By retaining more water in the soil and for a longer period of time, the treatment can increase plant tolerance to drought by (1) directly providing more water to plants thus increasing transpiration and (2) increasing the time available for metabolic adjustment for plants to better adapt to drier conditions. At the plant-soil interface, bacterial EPS and biofilm maintain soil water connectivity in ways similar to root mucilage that the filaments of EPS assist physical contact between root and soil particles and slow the drying process to insure continuous flow to roots. Rhizobacertia, when used to treat soil, may have a larger sphere of EPS influence compared to root mucilage as they are more mobile than plant roots, although *B. subtilis* cells were found to be unlikely to transport over long distances in sandy soils (Kinoshita et al., 1993). In addition, the shift of water consumption from soil evaporation to plant transpiration increases green water (i.e., the water stored in soil) availability and use efficiency. Along with *B. subtilis* UD1022's ability to fix nitrogen and increase phosphorus solubility, the treatment can trigger positive soil-water-plant feedbacks including increase in crop biomass or canopy size that leads to shading effects of the canopy, which then further decreases soil evaporation and induces a "vapor shift" from soil evaporation to transpiration, and ultimately to increased crop production. Therefore, application of PGPR represents a potentially viable technology and a soil-based and sustainable solution that can contribute to solving food security issues and providing for the growing population in the changing climate.

All documents, books, manuals, papers, patents, published patent applications, guides, abstracts, and/or other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed:

1. A soil composition, comprising at least 80 wt % soil particles having a particle size no greater than 2 mm and at least 0.1 wt % *Bacillus subtilis* UD1022 in an amount effective for reducing water evaporation rate of the soil composition, each based on the total weight of the soil composition, wherein at least 50% of the soil particles have a particle size in the range of 0.05-2 mm.

2. The soil composition of claim 1, wherein the *Bacillus subtilis* UD1022 is in an amount effective for increasing water content of the soil composition as compared with a control composition.

3. The soil composition of claim 1, wherein the *Bacillus subtilis* UD1022 is in an amount effective for reducing unsaturated hydraulic conductivity of the soil composition as compared with a control composition.

4. The soil composition of claim 1, wherein the at least 50 wt % of the soil particles have a particle size in the range of 1-2 mm.

5. The soil composition of claim 1, wherein the at least 50 wt % of the soil particles have a particle size in the range of 1-5 mm.

6. The soil composition of claim 1, wherein the at least 50 wt % of the soil particles have a particle size in the range of 0.25-0.5 mm.

7. The soil composition of claim 1, wherein the at least 50 wt % of the soil particles have a particle size in the range of 0.1-0.25 mm.

8. The soil composition of claim 1, wherein the at least 50 wt % of the soil particles have a particle size in the range of 0.05-0.1 mm.

9. The soil composition of claim 1, wherein the soil composition has a soil texture selected from the group consisting of sand, loamy sand, sandy loam, loam, silt loam and silt.

10. A method for reducing water evaporation rate of a soil composition, wherein the soil composition comprises at least 80 wt % soil particles having a particle size no more than 2 mm and at least 50% of the soil particles have a particle size in the range of 0.05-2 mm, comprising applying to the soil composition *Bacillus subtilis* UD1022 in an amount effective for reducing water evaporation rate of the soil composition.

11. The method of claim 10, further comprising increasing water content of the soil composition.

12. The method of claim 10, further comprising reducing unsaturated hydraulic conductivity of the soil composition.

13. The method of claim 10, wherein the at least 50 wt % of the particles have a particle size in the range of 1-2 mm.

14. The method of claim 10, wherein the at least 50 wt % of the particles have a particle size in the range of 0.5-1 mm.

15. The method of claim 10, wherein the at least 50 wt % of the particles have a particle size in the range of 0.25-0.5 mm.

16. The method of claim 10, wherein the at least 50 wt % of the particles have a particle size in the range of 0.1-0.25 mm.

17. The method of claim 10, wherein the at least 50 wt % of the particles have a particle size in the range of 0.05-0.1 mm.

\* \* \* \* \*